(12) United States Patent
Meyre et al.

(10) Patent No.: US 11,191,846 B2
(45) Date of Patent: Dec. 7, 2021

(54) METHODS OF TREATMENT UTILIZING BIOCOMPATIBLE NANOPARTICLES AND THERAPEUTIC AGENTS

(71) Applicant: CURADIGM SAS, Paris (FR)

(72) Inventors: Marie-Edith Meyre, Saint Mande (FR); Agnes Pottier, Paris (FR); Matthieu Germain, Champigny sur Marne (FR); Celine Berjaud, Paris (FR); Audrey Darmon, Alfortville (FR)

(73) Assignee: CURADIGM SAS, Paris (FR)

( * ) Notice: Subject to any disclaimer, the term of this patent is extended or adjusted under 35 U.S.C. 154(b) by 120 days.

(21) Appl. No.: 16/051,604

(22) Filed: Aug. 1, 2018

(65) Prior Publication Data

US 2018/0339062 A1 Nov. 29, 2018

Related U.S. Application Data

(63) Continuation of application No. 15/529,096, filed as application No. PCT/EP2015/077423 on Nov. 24, 2015, now abandoned.

(30) Foreign Application Priority Data

Nov. 25, 2014 (EP) ..................................... 14306871

(51) Int. Cl.
| | |
|---|---|
| *A61K 47/69* | (2017.01) |
| *A61K 47/68* | (2017.01) |
| *A61K 47/42* | (2017.01) |
| *A61K 9/50* | (2006.01) |
| *A61K 9/51* | (2006.01) |
| *C07K 16/22* | (2006.01) |

(52) U.S. Cl.
CPC ........ *A61K 47/6929* (2017.08); *A61K 9/5052* (2013.01); *A61K 9/51* (2013.01); *A61K 9/5169* (2013.01); *A61K 47/42* (2013.01); *A61K 47/6803* (2017.08); *A61K 47/6849* (2017.08); *A61K 47/6931* (2017.08); *C07K 16/22* (2013.01)

(58) Field of Classification Search
CPC ............ A61K 47/6929; A61K 47/6931; A61K 47/6803; A61K 47/6849; A61K 47/42; A61K 9/5052; A61K 9/51; A61K 9/5169; C07K 16/22
See application file for complete search history.

(56) References Cited

U.S. PATENT DOCUMENTS

| | | | |
|---|---|---|---|
| 6,117,454 A | 9/2000 | Kreuter et al. | |
| 7,276,477 B2 * | 10/2007 | Osslund | A61P 17/06 514/16.6 |
| 8,845,507 B2 | 9/2014 | Levy et al. | |
| 10,413,509 B2 * | 9/2019 | Pottier | A61K 9/0014 |
| 2011/0027375 A1 | 2/2011 | Tillement et al. | |
| 2013/0261061 A1 | 10/2013 | Acharya et al. | |
| 2014/0186447 A1 | 7/2014 | Desai | |
| 2014/0213765 A1 | 7/2014 | Lee | |
| 2016/0184225 A1 | 6/2016 | Pottier et al. | |
| 2016/0310614 A1 | 10/2016 | Pottier et al. | |
| 2017/0258717 A1 | 9/2017 | Germain et al. | |
| 2017/0258718 A1 | 9/2017 | Meyre et al. | |
| 2017/0258720 A1 | 9/2017 | Pottier et al. | |
| 2017/0258721 A1 | 9/2017 | Germain et al. | |
| 2019/0374465 A1 * | 12/2019 | Germain | A61K 31/704 |
| 2020/0009050 A1 * | 1/2020 | Pottier | A61K 9/127 |

FOREIGN PATENT DOCUMENTS

| | | |
|---|---|---|
| EP | 2 000 150 | 12/2008 |
| EP | 2 537 530 | 12/2012 |
| FR | 2 922 106 | 4/2009 |
| WO | WO 96/35415 | 11/1996 |
| WO | WO 2005/063305 | 7/2005 |
| WO | WO 2007/128066 | 11/2007 |

(Continued)

OTHER PUBLICATIONS

Chames et al., British Journal of Pharmacology, 157, pp. 220-233. (Year: 2009).*
Jolies, S., W. A. C. Sewell, and S. A. Misbah. "Clinical uses of intravenous immunoglobulin." Clinical and experimental immunology 142.1 (2005): 1-11. (Year: 2005).*
Holt, P. D. J. "Immunoglobulins in blood transfusion." Immunochemistry in Clinical Laboratory Medicine. Springer, Dordrecht, 1979. 99-113. (Year: 1979).*
Katragkou, Aspasia, Emmanuel Roilides, and Thomas J. Walsh. "Role of Immunoglobulin Therapy to Prevent and Treat Infections." Management of Infections in the Immunocompromised Host. Springer, Cham, 2018. 339-358. (Year: 2018).*

(Continued)

*Primary Examiner* — Abigail Vanhorn
(74) *Attorney, Agent, or Firm* — Saliwanchik, Lloyd & Eisenschenk (57) ABSTRACT

The invention pertains to a therapeutic, prophylactic or diagnostic method comprising, administering a pharmaceutical compound followed by administering a biocompatible nanoparticle comprising an oligomer of albumin, wherein the longest or largest dimension of the nanoparticle is between about 4 nm and about 500 nm. In preferred embodiments, administering the biocompatible nanoparticles is performed between more than 5 minutes and about 72 hours after administering the pharmaceutical compound. In particular embodiments, the pharmaceutical compound is a pharmaceutical antibody, such as a monoclonal antibody, a drug conjugated antibody, an engineered antibody and a multispecific antibody. According to the methods of the invention, administering the biocompatible nanoparticle comprising oligomers of albumin after administering the pharmaceutical compound maintains or increases the therapeutic benefit and reduces toxicity of the pharmaceutical compound when compared to the therapeutic benefit and toxicity induced by administering the pharmaceutical compound alone.

8 Claims, 6 Drawing Sheets

(56) References Cited

FOREIGN PATENT DOCUMENTS

| WO | WO 2009/105774 | 8/2009 |
|---|---|---|
| WO | WO 2009/147214 | 12/2009 |
| WO | WO 2010/048623 | 4/2010 |
| WO | WO 2011/070324 | 6/2011 |
| WO | WO 2011/119988 | 9/2011 |
| WO | WO 2012/051220 | 4/2012 |
| WO | WO 2012/104275 | 8/2012 |
| WO | WO 2012/104277 | 8/2012 |
| WO | WO 2014/057432 | 4/2014 |
| WO | WO 2015/091888 | 6/2015 |

OTHER PUBLICATIONS

Jiang, Hongpeng, et al. "Cancer IgG, a potential prognostic marker, promotes colorectal cancer progression." Chinese Journal of Cancer Research 31.3 (2019): 499. (Year: 2019).*

Relkin, Norman R., et al. "A phase 3 trial of IV immunoglobulin for Alzheimer disease." Neurology 88.18 (2017): 1768-1775. (Year: 2017).*

Winer, Daniel A., et al. "B cells promote insulin resistance through modulation of T cells and production of pathogenic IgG antibodies." Nature medicine 17.5 (2011): 610-617. (Year: 2011).*

St-Amour, Isabelle, et al. "Impact of intravenous immunoglobulin on the dopaminergic system and immune response in the acute MPTP mouse model of Parkinson's disease." Journal of neuroinflammation 9.1 (2012): 1-15. (Year: 2012).*

Gladwin, Mark T., and Vandana Sachdev. "Cardiovascular abnormalities in sickle cell disease." Journal of the American College of Cardiology 59.13 (2012): 1123-1133. (Year: 2012).*

Babcock, J. J. et al. "Bovine serum albumin oligomers in the E- and B-forms at low protein concentration and ionic strength" *International Journal of Biological Macromolecules*, Feb. 1, 2013, pp. 42-53, vol. 53.

Ma, P. et al. "Paclitaxel Nano-Delivery Systems: A Comprehensive Review" *Journal of Nanomedicine and Nanotechnology*, Jan. 1, 2013, pp. 1-16, vol. 4, No. 2.

Written Opinion in International Application No. PCT/EP2015/077423, dated Jan. 21, 2016, pp. 1-5.

Belisario, M. A. et al. "Effect of avarol, avarone and nine of their natural and synthetic derivatives on microsomal drug-metabolizing enzymes" *Toxicology Letters*, 1991, pp. 183-193, vol. 57.

Michalets, E. L. et al. "Update: Clinically Significant Cytochrome P-450 Drug Interactions" *Pharmacotherapy*, 1998, pp. 84-112, vol. 18, No. 1.

Written Opinion in International Application No. PCT/EP2015/077441, dated Feb. 3, 2016, pp. 1-6.

He, C. et al. "Effects of particle size and surface charge on cellular uptake and biodistribution of polymeric nanoparticles" *Biomaterials*, May 1, 2010, pp. 3657-3666, vol. 31, No. 13.

"NCL Method PCC-2 Measuring Zeta Potential of Nanoparticles" Nov. 1, 2009, Retrieved from the Internet: URL:http://ncl.cancer.gov/NCL_Method_PCC-2.pdf on Feb. 23, 2015, pp. 1-14.

Written Opinion in International Application No. PCT/EP2015/077446, dated Feb. 3, 2016, pp. 1-6.

Banquy, X. et al. "Effect of mechanical properties of hydrogel nanoparticles on macrophage cell uptake" *Soft Matter*, Jan. 1, 2009, pp. 3984-3991, vol. 5, No. 20.

Written Opinion in International Application No. PCT/EP2015/077438, dated Jan. 27, 2016, pp. 1-7.

Written Opinion in International Application No. PCT/EP2015/077425, dated Jan. 15, 2016, pp. 1-6.

DeKrafft, K.E. et al. "Zr- and Hf-based nanoscale metal-organic frameworks as contrast agents for computed tomography" *Journal of Materials Chemistry*, Sep. 21, 2012, pp. 18139-18144, vol. 22, No. 35.

Maggiorella, L. et al. "Nanoscale radiotherapy with hafnium oxide nanoparticles" *Future Oncology*, Sep. 1, 2012, pp. 1167-1181, vol. 8, No. 9.

Written Opinion in International Application No. PCT/EP2014/078619, dated Mar. 26, 2015, pp. 1-6.

Thompson, K. M. et al. "Human monoclonal antibodies specific for blood group antigens demonstrate multispecific properties characteristic of natural autoantibodies" *Immunology*, 1992, pp. 146-157, vol. 76.

Noizat-Pirenne, F. et al. "Rituximab for prevention of delayed hemolytic transfusion reaction in sickle cell disease" *Haematologica*, 2007, pp. e132-e135, vol. 92.

Liumbruno, G. et al. "Recommendations for the use of albumin and immunoglobulins" *Blood Transfus*, 2009, pp. 216-234, vol. 7.

Milojevic, J. et al. "Stoichiometry and Affinity of the Human Serum Albumin-Alzheimer's Aβ Peptide Interactions" *Biophysical Journal*, Jan. 2011, pp. 183-192, vol. 100.

* cited by examiner

METHODS OF TREATMENT UTILIZING BIOCOMPATIBLE NANOPARTICLES AND THERAPEUTIC AGENTS

CROSS-REFERENCE TO RELATED APPLICATION

This application is a continuation of U.S. application Ser. No. 15/529,096, filed May 24, 2017, which is the U.S. national stage application of International Patent Application No. PCT/EP2015/077423, filed Nov. 24, 2015.

FIELD OF THE INVENTION

The invention relates to a pharmaceutical composition comprising the combination of (i) at least one biocompatible nanoparticle, said biocompatible nanoparticle comprising at least one oligomer of albumin (n≥2) or consisting in an oligomer of albumin, and of (ii) at least one compound of interest, typically at least one pharmaceutical compound, to be administered to a subject in need of such at least one compound of interest, wherein the at least one nanoparticle potentiates the at least one compound of interest efficiency. The longest or largest dimension of the biocompatible nanoparticle is typically between about 4 and about 500 nm.

The invention also relates to such a composition for use for administering the at least one compound of interest in a subject in need thereof, wherein the at least one biocompatible nanoparticle and the at least one compound of interest are to be administered in said subject sequentially, typically between more than 5 minutes and about 72 hours from each other.

The combined, and typically sequential, administration to the subject of the at least one biocompatible nanoparticle and of the at least one compound of interest maintains, or even increases, the pharmaceutical (i.e., therapeutic, prophylactic or diagnostic) benefit of said at least one compound of interest for a reduced toxicity thereof in said subject when compared to the pharmaceutical benefit and toxicity induced by said at least one compound of interest when administered at the standard pharmaceutical dose in the absence of any biocompatible nanoparticle.

BACKGROUND

In order to ensure safety and efficacy, therapeutic compounds are required to be selectively delivered to their target site at an optimal rate in the subject in need thereof.

Pharmacokinetics (pK) is a branch of pharmacology dedicated to the determination of the fate of substances administered externally to a living organism. This determination involves steps of measuring compound's concentrations in all major tissues over a long enough period of time, preferably until the compound's elimination. Pharmacokinetics is necessary to efficiently describe the compound's behavior in vivo, including the mechanisms of its absorption and distribution as well as its chemical changes in the organism. The pK profile in the blood can be fitted using various programs to obtain key pK parameters that quantitatively describe how the body handles the compound. Important parameters include maximum concentration ($C_{max}$), half-life ($t_{1/2}$), clearance, area under curve (AUC), and mean resident time (MRT), i.e., the average time during which a compound stays in an organism. When a prolonged blood circulation of the compound formulation is observed, it is usually associated with an increased $t_{1/2}$, a reduced clearance, an increased AUC, and an increased MRT. pK data are often used in deciding the optimal dose and dose regimen for maintaining the desirable blood concentration in order to improve therapeutics' efficiency with minimal side effects. In addition, as is well-known by the skilled person, the blood concentration of a compound is correlated with both its efficacy and toxicity in most cases, typically for free drugs.

Figure 1:
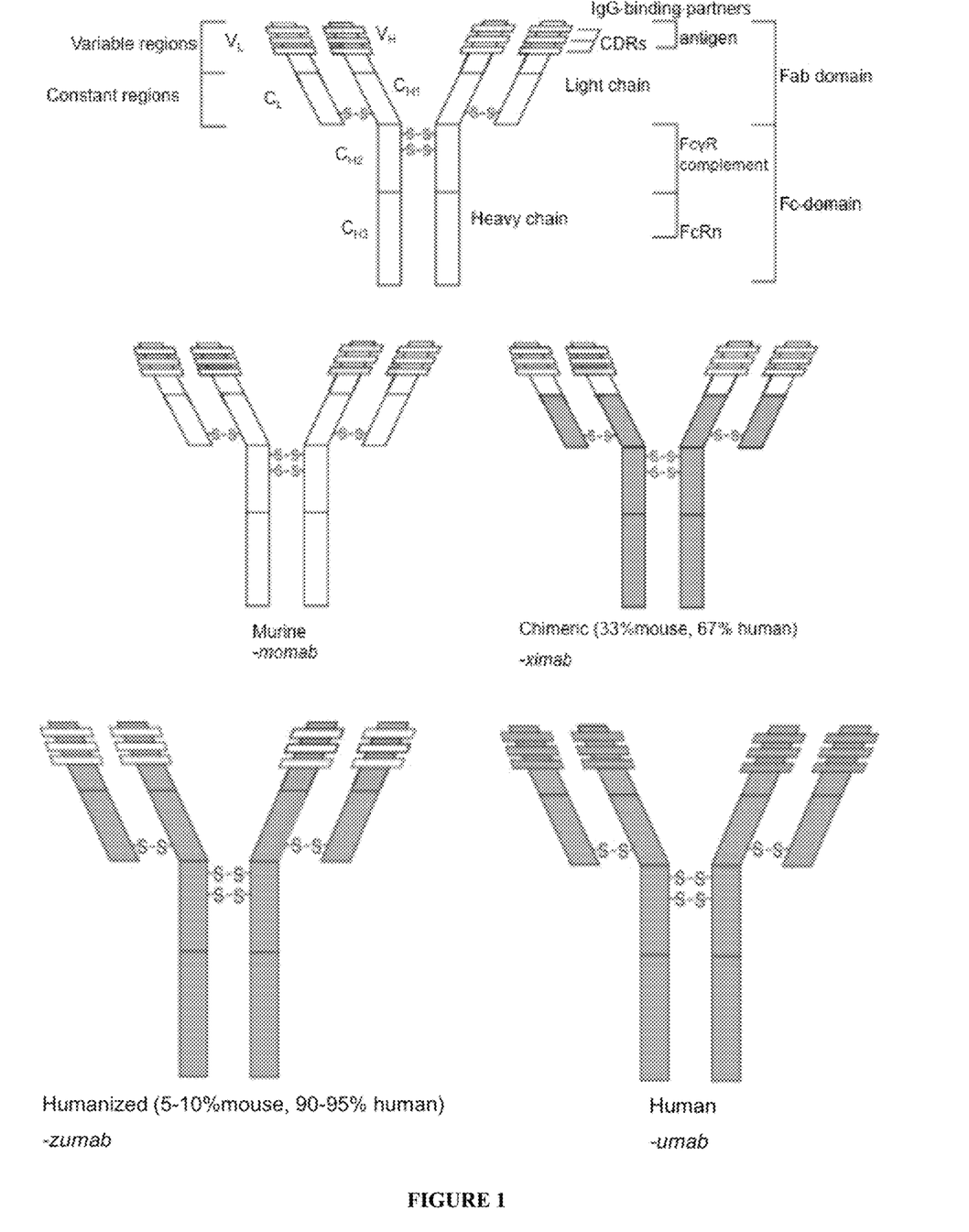
FIG. 1: Structure of IgG molecules [Pharmacokinetics, Pharmacodynamics and physiologically-based pharmacokinetic modelling of monoclonal antibodies. Dostalek M, Gardner I, Gurbaxani B M, Rose R H, Chetty M. Clin Pharmacokinet (2013) 52:83-124].

Monoclonal antibodies (mAbs) represent a growing segment of the development pipeline in the pharmaceutical industry. Many protein therapeutics, especially mAbs and functional derivatives (fusion proteins, fragments, etc.), have been approved as drugs in the US, Europe and Japan over the past 20 years. The number of mAbs under development is also large with estimates as high as 500 being reported [Pharmacokinetics, Pharmacodynamics and physiologically-based pharmacokinetic modelling of monoclonal antibodies. Dostalek M, Gardner I, Gurbaxani B M, Rose R H, Chetty M. Clin Pharmacokinet (2013) 52:83-124]. In humans there are five sub-classes of immunoglobulins (Ig), IgA, IgD, IgE, IgG and IgM, which differ with respect to their heavy chains but share the same light chains. IgG is the most prevalent immunoglobulin and represents 70-80% of the total immunoglobulin serum level. Based on the internal structure and the antigenic differences, the IgG sub-class can be divided into four main groups: IgG1, IgG2, IgG3 and IgG4. IgG molecules are constructed from two heavy chains (~50 kDa) and two light chains (~25 kDa) joined together by a polypeptide hinge region and a number of disulfide bridges forming a Y-like shaped protein consisting of two Fab (fragment antigen binding) domains and one Fc ("fragment crystallizable") domain (see FIG. 1).

The Fc region is associated with antibody elimination half-life ($t_{1/2}$), with intact IgG molecules having a longer $t_{1/2}$ than Fab fragment alone. The average $t_{1/2}$ of IgG1, IgG2 and IgG4 is approximately 21 days; whereas IgG3 has an average $t_{1/2}$ of 7.1 days. Although a majority of mAbs are selective in their target binding and bind only their specific soluble or cell-surface targets, some mAbs can bind to several different targets. The importance of this off-target binding can be seen in two different ways: (1) as a contribution to the primary activity of the drug; and (2) as a cause of adverse effects. Long circulating mAbs may indeed generate unwanted normal tissue toxicities.

Jaggi J. S. et al. ("*Improved tumor imaging and therapy via i. v. IgG-mediated time sequential modulation of neonatal receptor,*" The Journal of Clinical Investigation, Vol. 117, No. 9, 2007: 2422-2430) reported a therapeutic strategy to beneficially alter the pharmacokinetics of IgG antibodies via pharmacological inhibition of the neonatal Fr receptor (FcRn) using high-dose IgG therapy with some positive outcome.

Still, as is apparent from the prior art and despite a long medical need, the improvement of compounds (including therapeutic, prophylactic as well as diagnostic compounds) which cannot be efficiently used in patients due to their unacceptable toxicity or to their unfavorable pharmacokinetics parameters remains a concern.

DETAILED DESCRIPTION

The present invention now allows optimization of the efficiency of a compound of interest (herein also identified as "the compound" or as "the pharmaceutical compound") whatever its intended use in the context of therapy, prophylaxis or diagnostic. The composition herein described, which is a combination of (i) at least one biocompatible nanoparticle, said biocompatible nanoparticle comprising at least one oligomer of albumin (n≥2) or consisting of an oligomer of albumin, and (ii) at least one compound of interest, optimizes the at least one compound of interest pharmacokinetic parameters, and, as a consequence, now renders possible the development of therapeutic compounds which could not have been developed otherwise, typically due to their unacceptable toxicity. Typically, the biocompatible nanoparticle is not used as such a pharmaceutical compound, i.e., as a therapeutic, prophylactic or diagnostic compound.

Inventors surprisingly discovered that a biocompatible nanoparticle comprising at least one oligomer of albumin (n≥2) or consisting of an oligomer of albumin efficiently reduces unwanted normal tissue toxicities of antibody(ies) when said at least one oligomer of albumin and said antibody(ies) are administered sequentially, preferably when said at least one oligomer of albumin is administered after the antibody(ies) in a subject in need of said antibody compound.

A typical composition of the invention (herein generally identified as "pharmaceutical composition") is a composition comprising the combination of (i) at least one biocompatible nanoparticle, said biocompatible nanoparticle comprising at least one oligomer of albumin (n≥2) or consisting of an oligomer of albumin, and (ii) at least one compound ("the compound of interest"), wherein the longest or largest dimension of the biocompatible nanoparticle is typically between about 4 nm and about 500 nm.

Typically, the ratio between the (at least one) biocompatible nanoparticles and compounds of interest is between 0.1/1 and 1000/1 or 0.5/1 and 1000/1, preferably between 0.5/1 and 500/1, even more preferably between 0.5/1 and 300/1.

A preferred objet of a the invention is a pharmaceutical composition comprising the combination of (i) at least one biocompatible nanoparticle, said biocompatible nanoparticle comprising at least one oligomer of albumin (n≥2) or consisting of an oligomer of albumin, and (ii) at least one pharmaceutical compound, wherein the longest or largest dimension of the at least one biocompatible nanoparticle is between about 4 nm and about 500 nm, for use for administering the at least one pharmaceutical compound in a subject in need thereof, wherein the at least one nanoparticle and the at least one pharmaceutical compound are to be administered in a subject in need of said at least one pharmaceutical compound between more than 5 minutes and about 72 hours from each other, and wherein the biocompatible nanoparticle is not used as such as a pharmaceutical compound.

The terms "about" and "around" when associated to with value, such as a nanoparticle's size or a time interval, indicates that a variation of the indicated value, which would be recognized by the skilled person as small variation, does not substantially impact the properties of the subject matter it is associated with and that said subject matter remains in the spirit of the claimed invention.

The combined administration to the subject of the at least one biocompatible nanoparticle and of the at least one compound of interest, through the composition of the invention, typically allows (maintains) the same pharmaceutical (i.e., therapeutic, prophylactic or diagnostic) benefit of the at least one compound of interest for a reduced toxicity thereof for the subject, or increases the pharmaceutical benefit of the at least one compound of interest for a reduced toxicity thereof for the subject, when compared to pharmaceutical benefit and toxicity induced by the standard pharmaceutical dose of said at least one compound of interest in the absence of any biocompatible nanoparticle.

As the shape of the particle can influence its "biocompatibility", particles having a quite homogeneous shape are herein preferred. For pharmacokinetic reasons, nanoparticles being essentially spherical/round or ovoid in shape are thus preferred. Such a shape also favors the nanoparticle's interaction with or uptake by cells. Spherical/round shape is particularly preferred.

In the spirit of the invention, the term "nanoparticle" refers to a product with a size in the nanometer range, typically between about 1 nm and about 500 nm, preferably between about 4 nm and about 500 nm, between about 4 and about 400 nm, about 30 nm and about 300 nm, about 20 nm and about 300 nm, about 10 nm and about 300 nm, for example between about 4 nm and about 100 nm, for example between about 10 nm, 15 nm or 20 nm and about 100 nm, 200 nm, or 300 nm.

The terms "size of the nanoparticle", "largest size of the nanoparticle" and "longest size of the nanoparticle" herein typically refer to the "longest or largest dimension of the nanoparticle" or "diameter of the nanoparticle" when spherical/round or ovoid in shape. Transmission Electron Microscopy (TEM) or Cryo-TEM can be used to measure the size of the nanoparticle. As well, Dynamic Light Scattering (DLS) can be used to measure the hydrodynamic diameter of nanoparticles in solution. These two methods may further be used one after the other to compare the hydrodynamic diameter of a nanoparticle measured by DLS with the size of said nanoparticle measured by TEM or Cryo-TEM, in order to confirm said size. A preferred method is DLS (Ref. International Standard ISO22412, Particle Size Analysis—Dynamic Light Scattering, International Organisation for Standardisation (ISO) 2008).

The surface charge of a nanoparticle can be modulated and is typically determined by zeta potential measurements in an aqueous medium for a nanoparticle concentration between 0.2 and 10 g/L, for a pH between 6 and 8, and typically for electrolyte concentrations in the aqueous medium between 0.001 and 0.2 M, for example 0.01 M or 0.15 M.

Typically, the biocompatible nanoparticle of the present invention has an electronic surface charge of at least |10 mV|, i.e., below −10 mV or above +10 mV, for example below between −12 mV or −15 mV and −20 mV or above between +12 mV or +15 mV and +20 mV, typically below −15 mV or above +15 mV. Preferably, the biocompatible nanoparticle of the present invention has an absolute electronic surface charge value ("absolute surface charge value") of more than 10 mV, said charge being even more preferably a negative charge.

Figure 2:
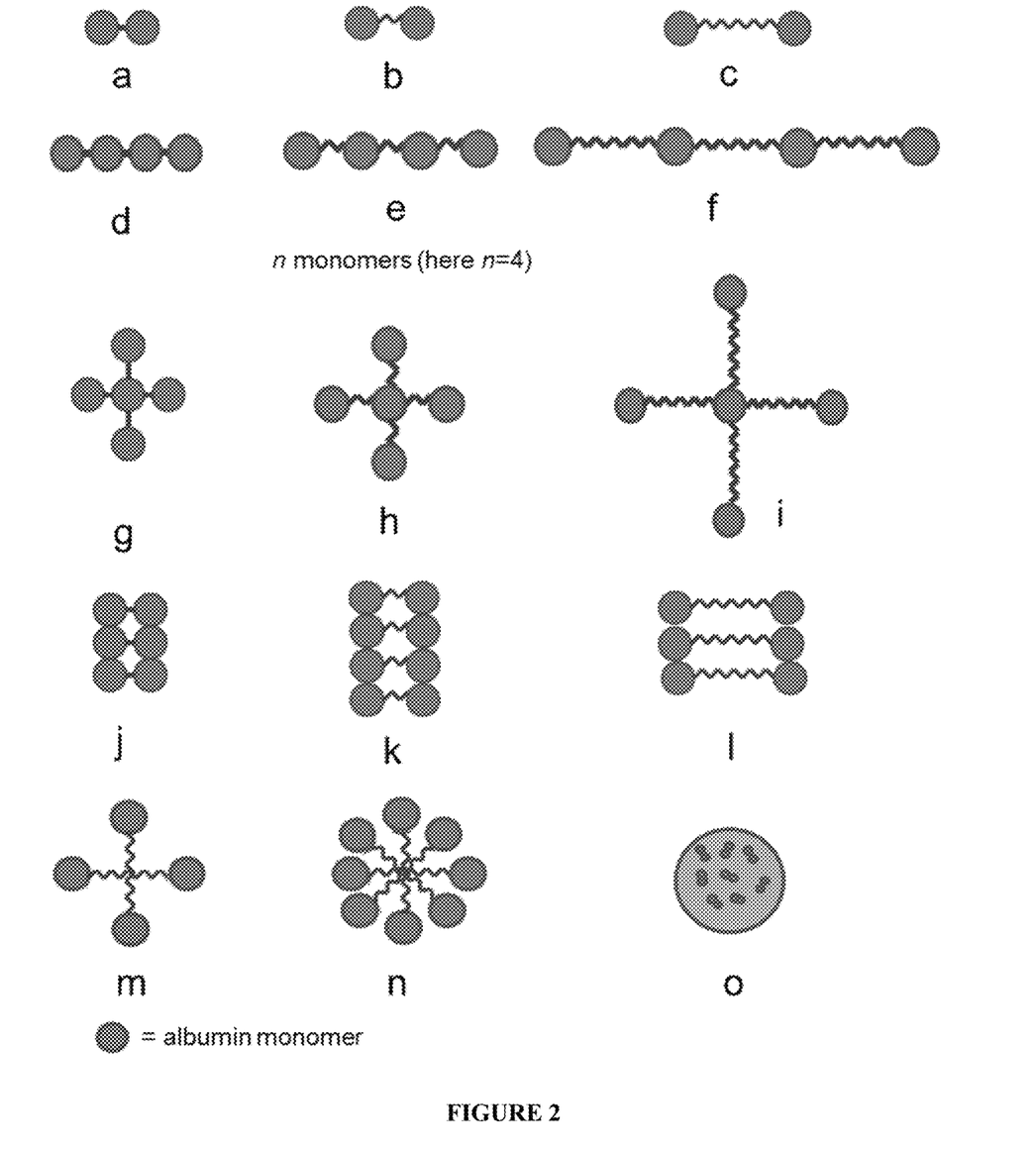
FIG. 2: Representation of the at least one biocompatible nanoparticle comprising, or consisting of, at least a dimer of albumin (a/b/c/–n=2) or an oligomer of albumin (d/e/f/g/h/i/j/k/l/m/n/o, n>2).

The at least one biocompatible nanoparticle of the invention comprises at least one oligomer of albumin (n≥2), for example a dimer (n=2) or a trimer (n=3) of albumin monomers or an oligomer of albumin comprising at least 4 monomers of albumin (n=4), or consisting of an oligomer of albumin (see FIG. 2). The at least one oligomer of albumin typically comprises at most 50 monomers of albumin, preferably less than 50 monomers of albumin, for example 30 monomers of albumin, preferably less than 25 monomers of albumin, for example 20 monomers of albumin.

Albumin monomers are typically conjugated to each other to form an albumin oligomer through direct interaction or via a linker.

The albumin molecule bears several functional groups that can be used to modify its reactivity and/or to crosslink multiple albumin molecules together [i.e., formation of dimers (n=2) or oligomers of more than two monomers of albumin (n>2)]. Most of the time, the crosslinking reaction consists of a nucleophile substitution. The crosslinking strategy may thus involve a step of "activation" of albumin, which consists of increasing the reactivity of the albumin molecule by grafting additional reactive groups, using a reagent [involving a group of interest such as a nucleophile group, i.e., a group that reacts with positively charged (or partially positive) atoms, or a leaving group, i.e., molecular fragment that departs with a pair of electrons in heterolytic bond cleavage], on the albumin molecule. The crosslinking reaction may occur (1) on the albumin molecule by coupling/crosslinking its available functional groups (primary amine, carboxylic acid or thiol) with a reactive linker (typically with a "short" linker having a molecular chain comprising less than 20 atoms, or with a "long" linker having a molecular chain comprising more than 20 atoms); or (2) on the "activated" albumin, with or without a linker.

Table 1 gives non exhaustive examples of strategies usable to graft reactive groups on the albumin molecule ("activation" step). Of note, any molecule bearing appropriate nucleophile or leaving groups may be involved in this "activation" step.

Table 2 gives non exhaustive examples of strategies usable to create a covalent bond between two albumin molecules ("crosslinking" step).

TABLE 1

Activation of albumin molecules

| Target group on albumin molecule | Reagent group | Examples of reagent | Reactive groups grafted on albumin |
|---|---|---|---|
| —S—S— | HS—R—SH | dithiothreitol, poly(ethylene glycol) dithiol | —SH |
| —NH$_2$ |  | 2-iminothiolane | —SH |
| —NH$_2$ | O=C—R—C=O + H$_2$N—R$_1$—S—S—R$_2$—NH$_2$ | glutaraldehyde + cystamine | —SH |
| —NH$_2$ | O=C—R—C=O + HS—R$_1$—NH$_2$ | glutaraldehyde + cysteamine | —SH |
| —COOH | R$_1$—N=C=N—R$_2$ + H$_2$N—R$_1$—S—S—R$_2$—NH$_2$ | ethylenediaminocarbodiimide + cystamine | —SH |
| —COOH | R$_1$—N=C=N—R$_2$ + HS—R$_1$—NH$_2$ | ethylenediaminocarbodiimide + cysteamine | —SH |
| —COOH | R$_1$—N=C=N—R$_2$ + HOOC—R$_1$(NH$_2$)—R$_2$(SH) | ethylenediaminocarbodiimide + cysteine | —SH |
| —NH$_2$ |  | N-hydroxysuccinimide-poly(ethylene glycol)-ortho-pyridyl disulfide (NHS-PEG-OPSS) |  |
| —NH$_2$ | X—R—COO—Y, where X = maleimide and Y = N-hydroxysuccinimide | 4-maleimidobutyric acid N-hydroxysuccinimide ester |  |
| —COOH | R$_1$—N=C=N—R$_2$ | ethylenediaminocarbodiimide |  |

TABLE 2

Crosslinking of albumin molecules to form oligomer (n ≥ 2) of albumin (● and ○ represent albumin monomers)

| Molecule 1 | Type of linker | Molecule 2 | Covalent bond |
|---|---|---|---|
| ●—SH | — | ○ with S—S ring | ○—S—S—● |
| ●—SH | X—R—X, where X = maleimide | ○—SH | ●—S—(succinimide)—N—R—N—(succinimide)—S—○ |
| ●—SH | Dibromo-maleimide | ○—SH | maleimide ring with ○—S and ●—S substituents |
| ● with guanidinium-O-C(=O)- group (R₁, R₂, HN, N) | X—R—X, where X = primary amine | ○ with guanidinium-O-C(=O)- group (R₁, R₂, HN, N) | ●—C(=O)—NH—R—NH—C(=O)—○ |
| ● with maleimide group | — | ○—SH | ●—N(succinimide)—S—○ |
| ● with maleimide group | X—R—X, where X = thiol | ○ with maleimide group | ●—N(succinimide)—S—R—S—(succinimide)N—○ |
| ●—NH₂ | X—R—X, where X = carboxylic acid, in the presence of EDC | ○—NH₂ | ●—NH—C(=O)—R—C(=O)—NH—○ |
| ●—NH₂ | X—OOC—R—COO—X, where X = N-hydroxy-succinimide | ○—NH₂ | ●—NH—C(=O)—R—C(=O)—NH—○ |
| ●—NH₂ | X—OOC—R—COO—X, where X = sulfo-N-hydroxy-sulfosuccinimide | ○—NH₂ | ●—NH—C(=O)—R—C(=O)—NH—○ |

TABLE 2-continued

Crosslinking of albumin molecules to form oligomer (n ≥ 2) of albumin (● and ○ represent albumin monomers)

| Molecule 1 | Type of linker | Molecule 2 | Covalent bond |
|---|---|---|---|
| ●—COOH | X—R—X, where X = alcohol | ○—COOH | ●—C(=O)—O—R—O—C(=O)—○ |

Oligomers (n≥2) of albumin by direct conjugation of albumin monomers (see FIGS. 2a, d and g) can for example be synthesized in the following manner:
  activation step (optional step): the albumin molecule/monomer can be thiolated using dithiothreitol (DDT) which reacts with the disulfide bond of said albumin molecule/monomer.
  Crosslinking or conjugation step: disulfide bonds are formed between several thiolated albumin molecules/monomers and/or between thiolated or non-thiolated albumin molecules/monomers resulting in oligomers of albumin.

Oligomers (n≥2) of albumin by conjugation of albumin monomers via a linker (in the following example the linker is either a "short" linker or a "long" linker) (see FIGS. 2b, e, h, and c, f, i, m, n) can for example be synthesized in the following manner:

Activation step (optional step):
The albumin molecule can typically be thiolated via an iminothiolane, or using a linker X—$R_1$—SH or $XR_1$—S—S—$R_2$X, wherein:
  X is a functional group reacting with the primary amine or the carboxylic group of the albumin molecule in presence or not of typically glutaraldehyde or Ethylenediaminocarbodiimide (EDC),
  $R_1$ or $R_2$ is a molecular chain comprising less than 20 atoms ("short" linker) or more than 20 atoms ("long" linker), and $R_1$ and $R_2$ are identical or different when grafted on the albumin molecule.
  Examples of linkers are Ethylenediaminocarbodiimide (EDC) and cysteine, EDC and cystamine, glutaraldehyde and cystamine.
  The albumin molecule can be functionalized with maleimide groups using a linker X—R—Y wherein:
  X is a maleimide group,
  R is a molecular chain with less than 20 atoms ("short" linker) or more than 20 atoms ("long" linker),
  Y is an N-hydroxysuccinimide (NHS) or a sulfo-N-hydroxysuccinimide (sulfoNHS) group.
  Examples of linkers are 4-maleimidobutyric acid N-hydroxysuccinimide ester.
  Crosslinking or conjugation step: typically, albumin molecules, thiolated albumin molecules and/or maleimide functionalized albumin molecules can be crosslinked or conjugated together, with or without a linker to form oligomers of albumins. Typical linkers to be used to form oligomers of albumins are presented in Table 2. Examples of linkers which can crosslink thiolated albumin molecules are crosslinkers comprising at least one maleimide group and can for example be a bismaleimide crosslinker such as bis(maleimido)ethane, 1,4-bis(maleimido)butane, 1,6-bis(maleimido)hexane, or 4arm-Poly (Ethylene glycol)-Maleimide, typically 4arm-Poly (Ethylene glycol)-Maleimide 11 kDa.

Association of monomers and/or oligomers of albumin can occur via hydrogen bonds, electrostatic and/or hydrophobic interactions (see FIGS. 2j, k and l).

Desolvation of albumin molecules and/or of oligomers of albumin by changing the polarity of the medium, i.e., by adding for instance different volumes of ethanol or acetone to an aqueous solution of albumin molecules and/or of oligomers of albumin, leads to the formation of larger nanoparticles of albumin (see FIG. 2o). Those larger nanoparticles of albumin may be further crosslinked to each other, typically using glutaraldehyde.

The combined administration of the biocompatible nanoparticle(s) together with the at least one compound of interest maintains, preferably increases, the pharmaceutical (i.e., therapeutic, prophylactic or diagnostic), typically therapeutic, benefit of the at least one compound of interest for a reduced toxicity thereof for the subject, typically when administered in the subject in need of the at least one compound of interest, between more than 5 minutes and about 72 hours from each other, when compared to the pharmaceutical benefit and toxicity induced by the standard pharmaceutical, typically therapeutic, dose of said at least one compound of interest in the absence of any biocompatible nanoparticle.

In a particular embodiment, the at least one biocompatible nanoparticle is administered with several compounds of interest, typically two compounds of interest.

Different molecules or agents can be used according to the present teaching as the compound of interest, typically as the at least one pharmaceutical compound of interest, administered in combination with at least one biocompatible nanoparticle as described hereinabove. This compound may be a therapeutic, a prophylactic or a diagnostic compound as previously explained. It is typically a compound known by the skilled person to be more or less toxic for a human being. The compound of interest can be radiolabelled.

The compound of interest is typically a pharmaceutical (therapeutic or diagnostic) compound, and in particular an antibody or a pharmaceutical compound comprising or consisting of at least one antibody, for example a combination of at least two antibodies or three antibodies. The antibody can be selected for example from a monoclonal antibody (mAb), an antibody-drug conjugate (which consists of a cytotoxic agent attached to the mAb via chemical linker), an engineered antibody, typically a glycoengineered mAb and a multispecific antibody.

A preferred compound of interest is an IgG-based compound, i.e., a compound comprising all or part of an IgG, or a combination of IgG-based compounds. The IgG-based compound of interest can for example be selected from Abatacept (fusion protein), Abciximab (Chimeric IgG1

Fab), adalimumab (Human IgG1), Aflibercept (fusion protein), Alefacept (fusion protein), Alemtuzumab (Humanized IgG1), Basiliximab (Chimeric IgG1), Belimumab (Human IgG1), Bevacizumab (Humanized IgG1), Brentuximab (Chimeric IgG1), canakinumab (Human IgG1), Certolizumab pegol (Humanized Fab fragment), Cetuximab (Human/murine chimeric IgG1), Daclizumab (Humanized IgG1), Denosumab (Human IgG2), Eculizumab (Humanized IgG2/4), Efalizumab (Humanized IgG1), Etanercept (Fusion protein), Gemtuzumab ozogamicin (Humanized IgG4), Golimumab (Human IgG1), Infliximab (Human IgG1/murine chimeric), Ipilimumab (Human IgG1), Natalizumab (Humanized IgG4), Ofatumumab (Humanized IgG1), Omalizumab (Humanized IgG1), Palivizumab (Humanized IgG1), Panitumumab (Human IgG2), Ranitumumab (Humanized IgG1 Fab), Rituximab (Chimeric IgG1), Tocilizumab (Humanized IgG1), Trastuzumab (Humanized IgG1), Ustekinumab (Human IgG1), and any other antibody of interest known by the physician to be usable to prevent or treat a disease as herein identified.

The pharmaceutical composition of the invention as claimed can be used in many fields, in particular in human and veterinary medicine. This composition is typically for use in an animal, preferably in a mammal (for example in the context of veterinary medicine), even more preferably in a human being whatever its age or sex.

The pharmaceutical compositions of the invention can be used to prevent or treat a disease or disorder selected from a cardiovascular disease, a Central Nervous System (CNS) disease, a gastrointestinal disease, a genetic disorder, a hematological disorder, a hormonal disorder, a disorder of the immune system, an infectious disease, a metabolic disorder, a musculoskeletal disorder, a cancer, a respiratory disease, an intoxication, etc. In a preferred embodiment, the pharmaceutical composition is for use to prevent or treat a disease or disorder selected from a cardiovascular disease, a CNS disease, a cancer, an infectious disease and a metabolic disorder.

In the context of the present invention, the at least biocompatible nanoparticle and the at least one compound of interest are advantageously to be administered in a subject in need of said compound of interest between more than 5 minutes and about 72 hours from each other, typically between more than 5 minutes and about 48 hours, preferably between more than 4 hours and about 48 hours, for example between more than 4 hours and about 24 hours, in order to optimize the at least one compound's pharmaceutical efficacy.

Also herein described is a method for treating a subject suffering from a disease such as those herein mentioned, wherein said method comprises administering to said subject a pharmaceutical composition of the invention, typically at least one biocompatible nanoparticle and at least one compound of interest as herein described. Any one of the at least one biocompatible nanoparticle or at least one compound of interest can be administered first to the subject as long as the biocompatible nanoparticle and the compound are administered between more than 5 minutes and about 72 hours from each other or according to any other herein described schedule. Preferably the at least one compound of interest is administered first to the subject (or in other words, the at least one biocompatible nanoparticle is administered after the at least one compound of interest). Administration of any of said at least one nanoparticle or at least one compound of interest can be a single administration of each, repeated administrations of each, for example several consecutive administrations of each. The at least one biocompatible nanoparticle may be administered once and the at least one compound of interest may be administered more than once and vice versa.

In a particular embodiment, the at least one biocompatible nanoparticle is at least administered at the beginning of a protocol comprising several administrations of at least one compound of interest, i.e., at least at the first administration of said at least one compound of interest and before or preferably after the administration of said at least one compound of interest.

In another particular embodiment, the at least one biocompatible nanoparticle is not administered at the beginning of a protocol comprising several administrations of at least one compound of interest and is not administered before the second or third administration of said at least one compound of interest, and before or preferably after the administration of said at least one compound of interest.

In the context of these last two embodiments, the at least one biocompatible nanoparticle can also be administered together (before or preferably after as previously explained) with the at least one compound of interest during part or all of the subsequent administrations of said at least one compound of interest.

The biocompatible nanoparticle(s) of the pharmaceutical composition of the invention can be administered by different routes such as subcutaneous, intra venous (IV), intra-dermic, intra-arterial, airway (inhalation), intra peritoneal, intra muscular and/or oral route (per os). Preferred routes are intra venous (IV), intra-arterial, and/or intra peritoneal.

The compound(s) of interest of the pharmaceutical composition of the invention can be administered by different routes such as subcutaneous, intra venous (IV), intra-dermic, intra-arterial, airway (inhalation), intra peritoneal, intra muscular and/or oral route (per os).

The following examples illustrate the invention without limiting its scope.

EXAMPLES

Example 1

Synthesis of the at Least One Biocompatible Nanoparticle Consisting of at Least an Oligomer (n≥2) of Albumin, for Example a Dimer (n=2) of Albumin, with Mean Particle Size Typically Below 50 nm Mouse serum albumin (1 g) was dissolved in 77 mL of 100 mM phosphate-buffered saline (PBS) pH8.5. The solution was mixed with 77 mL of a freshly aqueous 2-iminothiolane (reagent) solution (3 mM). After adjusting the pH to 8.5 with sodium hydroxide solution (NaOH), the suspension was incubated at room temperature during 48 h.

Subsequently, the resulting suspension was diluted in phosphate buffer and adjusted to pH 7.3. Elimination of excess reagent was performed and re-concentration of the as prepared suspension was achieved using a polyethersulfone membrane (50 kDa). Final concentration of albumin was determined using the Bradford method and found equal to about 65 g/L.

Example 2

Characterization of the at Least One Biocompatible Nanoparticle Consisting of an Oligomer of Albumin, for Example a Dimer (n=2) of Albumin in the Suspension of Example 1

Presence of nanoparticles consisting of at least an oligomer of albumin was checked by electrophoresis. 7.54, of suspension of mouse serum albumin (MSA) (albumin 0.5 g/L), or of suspension from Example 1 (albumin 0.5 g/L) were mixed with 2.5 µL of a solution of Lithium Dodecyl Sulfate (LDS) sample loading buffer (4×). A non-denaturating 4-12% gradient polyacrylamide gel was cast in the XCell SureLock vertical electrophoresis and run at 200V for 1h50. Typically, the proportion of oligomer is evaluated by separation by size exclusion chromatography on a superose 6 column followed by subsequent dosage of albumin in each fraction with the Bradford method, size evaluation in each fraction by dynamic light scattering (DLS) and molecular weight evaluation on each fraction by gel electrophoresis on a non-denaturating 4-12% gradient polyacrylamide gel.

Figure 3:
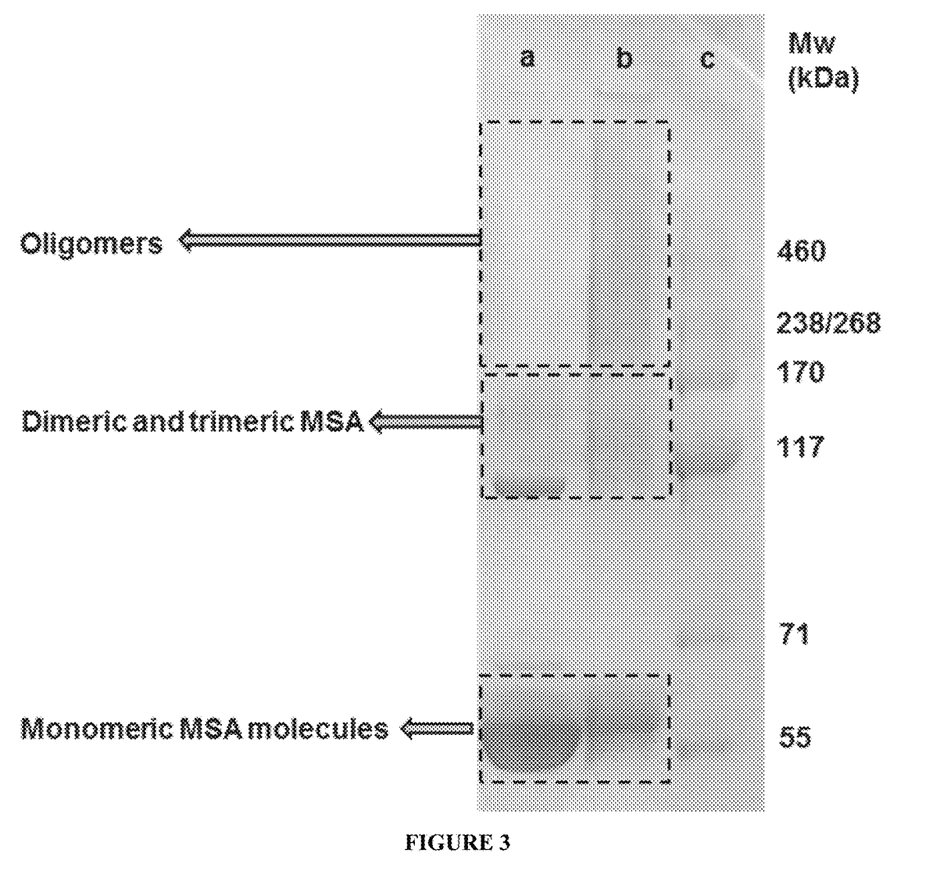
FIG. 3: Gradient polyacrylamide electrophoresis gel with:
 (a): a suspension of mouse serum albumin (MSA), i.e., a suspension of biocompatible nanoparticles No. 1;
 (b): a suspension of MSA prepared according to example 1, i.e., a suspension of biocompatible nanoparticles No. 2; and
 (c): HiMark Protein standard 31-460 kDa.

The results presented in FIG. 3 show that:
the MSA suspension (FIG. 3, line a) as such contains a low fraction of oligomers (n≥2) of albumin (suspension of biocompatible nanoparticles No. 1). About 10% of the collected albumin was identified as oligomers of albumin with molecular weights equal to about 120 kDa (n=2) (of note albumin monomer molecular weight is equal to about 66 kDa). The mean particle size of the biocompatible nanoparticles in suspension was measured by dynamic light scattering (DLS) using a zetasizer NanoZS (Malvern 5 Instrument) with a 633 nm HeNe laser at an angle of 173°. The mean particle size of the biocompatible nanoparticles in suspension was equal to about 9 nm with a polydispersity index (PDI) of 0.207.

The suspension from Example 1 (FIG. 3, line b) contains a larger proportion of oligomers of albumin (suspension of biocompatible nanoparticles No. 2) when compared to the MSA suspension. About 50% of the collected albumin was identified as oligomers of albumin with molecular weights comprised between about 120 kDa (n=2) and about 1300 kDa (n=20) (of note albumin monomer molecular weight is equal to about 66 kDa). The mean particle size of the biocompatible nanoparticles in suspension was measured by dynamic light scattering (DLS) using a zetasizer NanoZS (Malvern Instrument) with a 633 nm HeNe laser at an angle of 173°. The mean particle size of the biocompatible nanoparticles in suspension was equal to about 30 nm with a polydispersity index (PDI) of 0.250.

For the in vivo experiments described in Examples 4 and 5, both suspensions of biocompatible nanoparticles No. 1 and No. 2 were used to prepare the pharmaceutical composition comprising the combination of (i) at least one biocompatible nanoparticle, said biocompatible nanoparticle comprising at least one oligomer of albumin (n≥2) or consisting of an oligomer of albumin, and (ii) a pharmaceutical compound of interest.

Example 3

Preparation of the at Least One Biocompatible Nanoparticle, Said Biocompatible Nanoparticle Comprising at Least One Oligomer of Albumin (n≥2) (See FIG. 2m) or Consisting of an Oligomer of Albumin (See FIGS. 2a-l), with Mean Particle Size Typically Above 50 nm The albumin nanoparticles were prepared by the desolvation technique (*desolvation process and surface characterization of protein nanoparticles*. C. Weber, C. Coester, J. Kreuter, K. Langer, International Journal of Pharmaceutics, V 194; 2000; pp 91-102).

Figure 4:
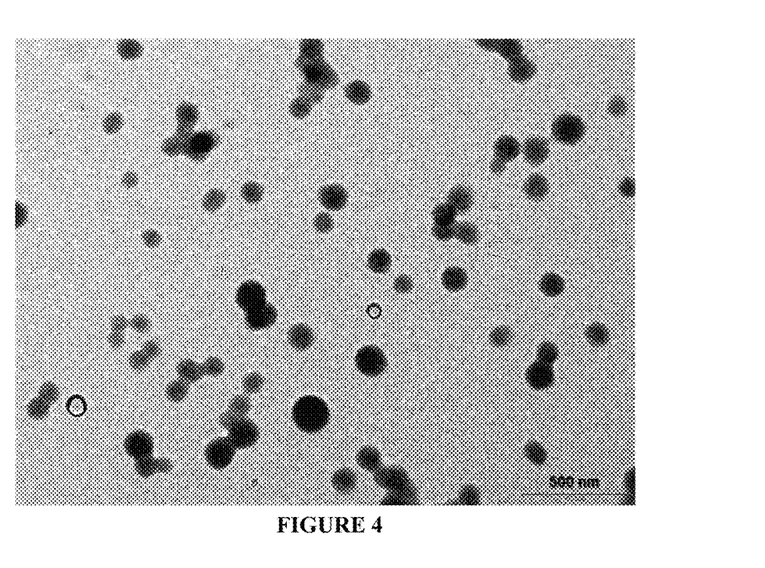
FIG. 4: Transmission electron microscopy (TEM) images of biocompatible nanoparticles comprising at least one oligomer of albumin (n≥2) or consisting of an oligomer of albumin, with mean particle size typically above 50 nm (scale bar 500 nm).

Bovine serum albumin (BSA) (100 mg) was dissolved in 2 mL distilled water at pH 7. A desolvating agent, acetone (5 mL), was added dropwise into the BSA solution, until the solution became turbid. The solution was stirred overnight. The solvent was subsequently eliminated by evaporation. The albumin nanoparticles were observed by Transmission Electronic Microscopy using JEOL JEM 100CX II HR (see FIG. 4).

Example 4

Tumor Re-Growth Delay of the Pharmaceutical Composition Comprising the Biocompatible Nanoparticles from Example 1 and the DC101 Compound in FaDu Xenografts (Mean RTV±SD)

This study was performed to investigate the efficacy of the pharmaceutical composition comprising the biocompatible nanoparticles from Example 1 and DC101 (rat anti-mouse VEGF receptor 2 monoclonal antibody that replaces Bevacizumab (Avastin®) for mice studies) as the therapeutic compound of interest, in FaDu tumor model xenografted on NMRI nude mice.

The human pharyngeal carcinoma FaDu cell line was purchased from LGC Standard (Molsheim, France). Cells were cultured in Eagle's Minimum Essential Medium supplemented with 10% fetal bovine serum (Gibco), with 5% $CO_2$.

NMRI nude mice, 6-7 weeks (20-25 g) were ordered from Janvier Labs (France). The mice were maintained under specific pathogen free conditions (sterilized food and water available ad libitum) and kept one week for acclimatization before starting the experiment.

FaDu tumors were obtained by subcutaneous injection of $2.10^6$ cells in 50 μL in the lower right flank of the mouse. The tumors were grown until reaching volume around about 100 mm³. Tumor diameters were measured using digital caliper and the tumor volume in mm³ was calculated using the following formula:

$$\text{Tumor volume (mm}^3\text{)} = \frac{\text{length (mm)} \times (\text{width})^2 (\text{mm}^2)}{2}$$

Figure 5:
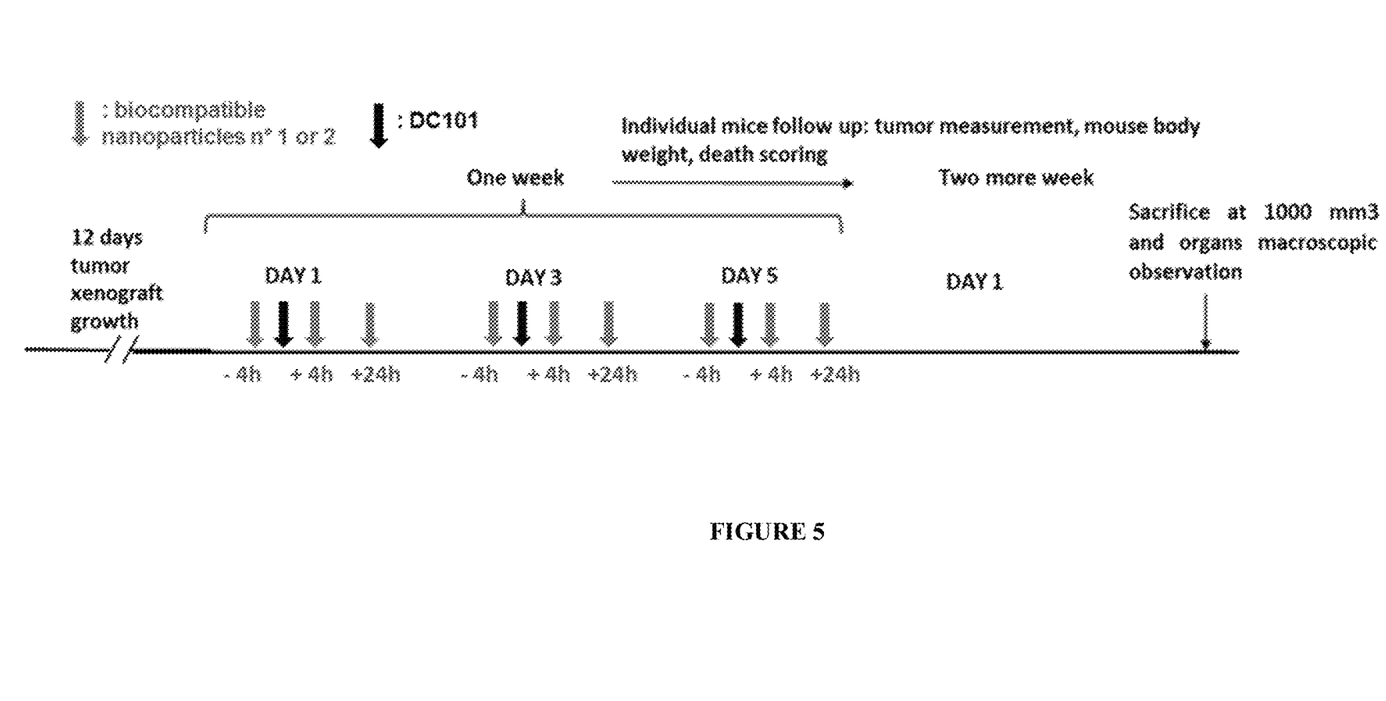
FIG. 5: Schematic representation of the treatment schedule for the pharmaceutical composition comprising (i) the biocompatible nanoparticles from example 1 (i.e., the suspension of biocompatible nanoparticles No. 1 or the suspension of biocompatible nanoparticles No. 2) and (ii) the DC101 compound in FaDu xenografts.

Mice were randomized into separate cages and identified by a number (paw tattoo). Seven groups were treated as illustrated in FIG. 5 and Table 3.

Group 1: Sterile NaCl 0.9% (control vehicle group).

Five (5) mice were intraperitoneally (IP) injected with a sterile NaCl 0.9% solution (volume equivalent to DC101 injection) on day 1, day 3 and day 5 each week during three consecutive weeks.

Group 2: DC101 at 800 μg/dose (treatment group).

Five (5) mice were intraperitoneally (IP) injected with a sterile DC101 solution (800 μg/dose) on day 1, day 3 and day 5 each week during three consecutive weeks.

Group 3: Pharmaceutical composition, i.e., the combination of the biocompatible nanoparticles No. 2 (65 g/L: 10 mL/kg of animal) and of DC101 (800 μg/dose) (treatment group).

Five (5) mice were intraperitoneally (IP) injected with a sterile DC101 solution (800 μg/dose) on day 1, day 3 and day 5 each week during three consecutive weeks. Each time (day), the intravenous (IV) injection of sterile suspension of biocompatible nanoparticles No. 2 was performed 4 hours before the injection of DC101.

Group 4: Pharmaceutical composition, i.e., the combination of the biocompatible nanoparticles No. 2 (65 g/L: 10 mL/kg of animal) and of DC101 (800 μg/dose) (treatment group).

Five (5) mice were intraperitoneally (IP) injected with a sterile DC101 solution (800 μg/dose) on day 1, day 3 and day 5 each week during three consecutive weeks. Each time (day), the intravenous (IV) injection of sterile suspension of biocompatible nanoparticles No. 2 was performed 4 hours after the injection of DC101.

TABLE 3

Schedule and dose conditions for the control groups (group 1: vehicle NaCl 0.9%; group 6: biocompatible nanoparticles No. 2) and the treatment groups (group 2: DC101 alone; group 3: injection of biocompatible nanoparticles No. 2 4 h before DC101; group 4: injection of biocompatible nanoparticles No. 2 4 h after DC101; group 5: injection of biocompatible nanoparticles No. 2 24 h after DC101; group 7: injection of biocompatible nanoparticles No. 1 4 h after DC101).

| Groups | Treatment | Mice number/ group | DC101 Adm. route | DC101 Adm. Volume (dose/adm.) | DC101 Treatment schedule | Biocompatible nanoparticles from example 1 injection schedule | biocompatible nanoparticles from example 1 (dose/adm) |
|---|---|---|---|---|---|---|---|
| 1 | 0.9% NaCl | 5 | IP | Equivalent to treatment | 1 injection at Days 1-3 and 5 for 3 weeks | — | — |
| 2 | DC101 alone | 5 | IP | 800 μg/dose | 1 injection at Days 1-3 and 5 for 3 weeks | | |
| 3 | DC101 + biocompatible nanoparticles No. 2, 4 h before | 5 | IP | 800 μg/dose | 1 injection at Days 1-3 and 5 for 3 weeks | IV injection 4 h before treatment adm at D1-D3-D5 for 3 weeks | 10 ml/kg |
| 4 | DC101 + biocompatible nanoparticles No. 2, 4 h after | 5 | IP | 800 μg/dose | 1 injection at Days 1-3 and 5 for 3 weeks | IV injection 4 h after treatment adm at D1-D3-D5 for 3 weeks | 10 ml/kg |
| 5 | DC101 + biocompatible nanoparticles No. 2, 24 h after | 5 | IP | 800 μg/dose | 1 injection at Days 1-3 and 5 for 3 weeks | IV injection 24 h after treatment adm at D1-D3-D5 for 3 weeks | 10 ml/kg |
| 6 | biocompatible nanoparticles No. 2 | 5 | | | | IV injection in the same timing as group 4 with adm at D1-D3-D5 for 3 weeks | 10 mL/kg |
| 7 | DC101 + biocompatible nanoparticles No. 1, 4 h after | 4 | IP | 800 μg/dose | 1 injection at Days 1-3 and 5 for 3 weeks | IV injection 4 h after treatment adm at D1-D3-D5 for 3 weeks | 10 ml/kg |

Group 5: Pharmaceutical composition, i.e., the combination of the biocompatible nanoparticles No. 2 (65 g/L: 10 mL/kg of animal) and of DC101 (800 µg/dose) (treatment group).

Five (5) mice were intraperitoneally (IP) injected with a sterile DC101 solution (800 µg/dose) on day 1, day 3 and day 5 each week during three consecutive weeks. Each time (day), the intravenous (IV) injection of sterile suspension of biocompatible nanoparticles No. 2 was performed 24 hours after the injection of DC101.

Group 6: Biocompatible nanoparticles No. 2 (65 g/L: 10 mL/kg of animal) (control group).

Five (5) mice were intravenously (IV) injected with a sterile suspension of biocompatible nanoparticles No. 2 (65 g/L: 10 mL/kg of animal) on day 1, day 3 and day 5 each week during three consecutive weeks.

Group 7: Pharmaceutical composition, i.e., the combination of the biocompatible nanoparticles No. 1 (65 g/L: 10 mL/kg of animal) and of DC101 (800 µg/dose) (treatment group).

Four (4) mice were intraperitoneally (IP) injected with a sterile DC101 solution (800 µg/dose) on day 1, day 3 and day 5 each week during three consecutive weeks. Each time (day), the intravenous (IV) injection of sterile suspension of biocompatible nanoparticles No. 1 was performed 4 hours after the injection of DC101.

DC101 product (BioXcell—4.83 mg/ml at pH 7, in PBS) was diluted at 4.6 mg/mL in NaCl 0.9% before injection of 1744, to obtain a dose of 800 µg per injection.

Suspension of biocompatible nanoparticles No. 1 and suspension of biocompatible nanoparticles No. 2 (Albumin content equal 65 g/L in PBS buffer) from Example 1 were injected without additional dilution at 10 mL/kg of animal.

DC101 was administrated by intraperitoneal injection (IP) with a 100U (0.3 ml) insulin syringe with a 29G needle (TERUMO, France). Suspension of biocompatible nanoparticles No. 1 and suspension of biocompatible nanoparticles No. 2 from Example 1 were injected by intravenous (IV) injection via lateral tail vein with a 1 mL syringe with a 26G needle (TERUMO, France).

Mice were followed up for clinical signs, body weight and tumor size.

Figure 6:
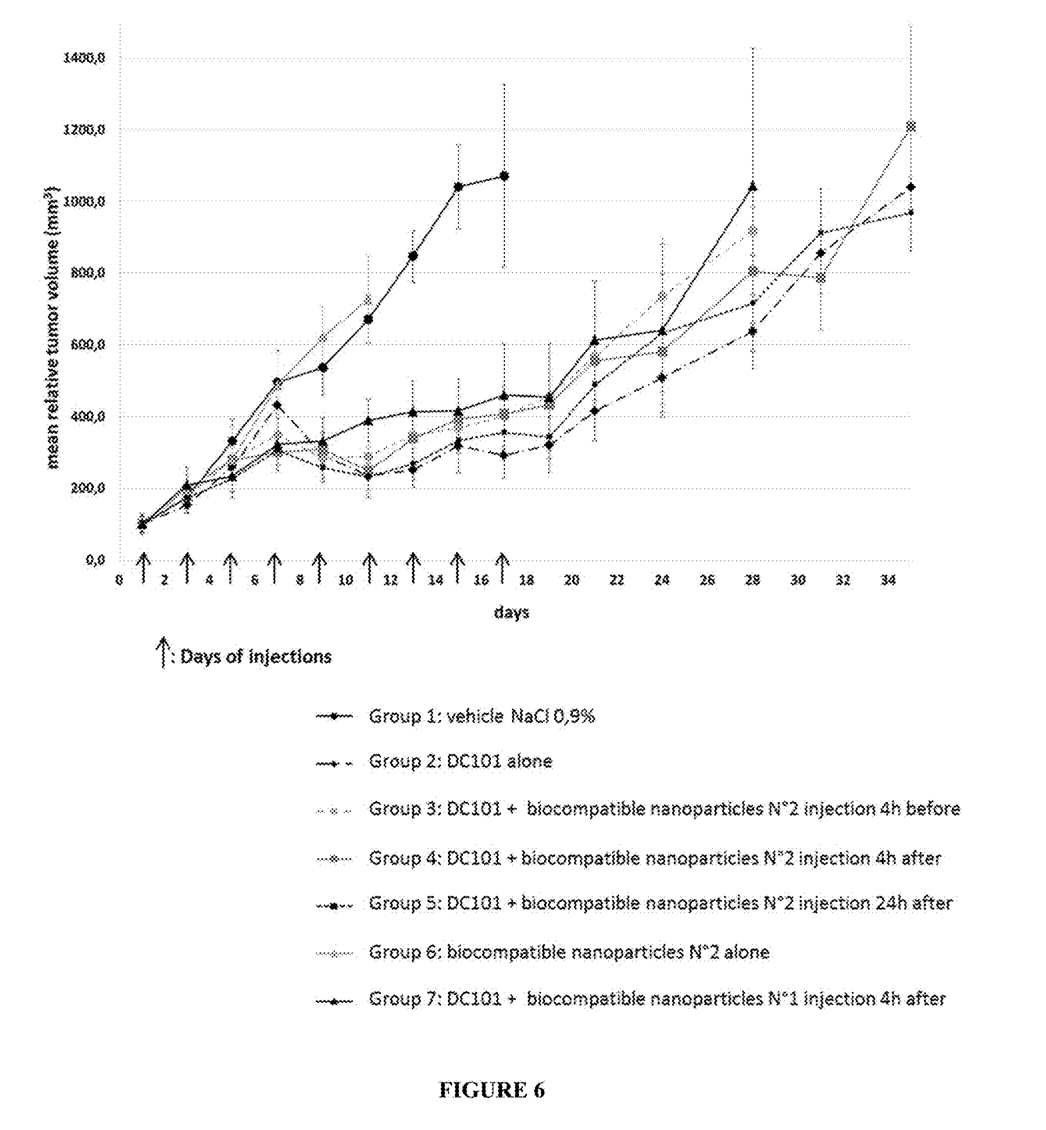
FIG. 6: Tumor re-growth delay of the pharmaceutical composition comprising the biocompatible nanoparticles from example 1 and the DC101 compound in FaDu xenografts (mean RTV±SD).

FIG. 6 shows the mean relative tumor volume (mean RTV) for all groups as obtained (in the conditions previously described) after injections of:

Vehicle (sterile NaCl 0.9%) intraperitoneally injected on days 1, 3 and 5 of each week during 3 consecutive weeks (group 1);
DC101 (800 µg/dose) intraperitoneally injected on days 1, 3 and 5 of each week during 3 consecutive weeks (group 2);
DC101 (800 µg/dose) intraperitoneally injected on days 1, 3 and 5 of each week during 3 consecutive weeks with biocompatible nanoparticles of suspension No. 2 intravenously injected 4 hours before DC101 injection (group 3);
DC101 (800 µg/dose) intraperitoneally injected on days 1, 3 and 5 of each week during 3 consecutive weeks with biocompatible nanoparticles of suspension No. 2 intravenously injected 4 hours after DC101 injection (group 4);
DC101 (800 µg/dose) intraperitoneally injected on days 1, 3 and 5 of each week during 3 consecutive weeks with biocompatible nanoparticles of suspension No. 2 intravenously injected 24 hours after DC101 injection (group 5);
Biocompatible nanoparticles No. 2 intravenously injected on days 1, 3 and 5 of each week during 3 consecutive weeks (group 6); and
DC101 (800 µg/dose) intraperitoneally injected on days 1, 3 and 5 of each week during 3 consecutive weeks with biocompatible nanoparticles of suspension No. 1 intravenously injected 4 hours after DC101 injection (group 7).

As shown in FIG. 6, a marked tumor growth inhibition is observed after 7 days of treatment for the groups including DC101 alone (group 2) or in combination with biocompatible nanoparticles of suspension No. 2 (groups 3, 4, 5) or in combination with biocompatible nanoparticle of suspension No. 1 (group 7), when compared to vehicle group (group 1) and biocompatible nanoparticles of suspension No. 2 (group 6). This marked tumor growth inhibition is similar between groups 2, 3, 4, 5 and 7.

Overall, those results show that the tumor growth delay obtained by DC101 treatment is not modified when using the pharmaceutical composition of the present invention (corresponding to the combination of the biocompatible nanoparticles from Example 1 and of the DC101 (800 µg/dose)). This tumor growth delay was observed when the biocompatible nanoparticles from Example 1 and the compound of interest (the DC101) were administered sequentially.

Example 5

Toxicity Evaluation of the Pharmaceutical Composition Comprising the Biocompatible Nanoparticles from Example 1 and the DC101 Antibody in FaDu Xenografts This study was performed to investigate the impact of the combination of the biocompatible nanoparticles from Example 1 with DC101 (rat anti-mouse VEGF receptor 2 monoclonal antibody that replaces Bevacizumab (Avastin®) for mice studies) on the toxicity of the DC101 treatment on FaDu tumor model xenografted on NMRI nude mice from Example 4.

Each mouse of the different groups (groups 1 to 7) of the tumor growth delay experiment (Example 4) was necropsied after mouse euthanasia when tumor volume exceeded 1000 mm$^3$ or presented any sign of necrosis. For each mouse, the following organs were observed during the necropsy for any sign of toxicity: liver, spleen, kidneys, skin, brain, stomach, intestines, lungs and heart. Table 4 shows the observations made during the necropsy of mice for each group from Example 4.

TABLE 4

Observations at necropsy made on the different groups of mice from Example 4.

| Group | observations |
| --- | --- |
| group 1: 0.9% NaCl (5 mice) | All organs were normal during necropsy for 5/5 mice |
| group 2: DC101 alone (5 mice) | Compared to control group (group 1): kidneys were colorless (clear brown) for 5/5 mice a splenomegaly was present for 3/5 mice liver was colorless (clear brown) for 2/5 mice other organs (intestines, heart, skin, lungs, stomach, brain) were similar to control group |

TABLE 4-continued

Observations at necropsy made on the different groups of mice from Example 4.

| Group | observations |
|---|---|
| group 3: DC101 + biocompatible nanoparticles No. 2, injection 4 h before (5 mice) | Compared to control group (group 1): kidneys were colorless (clear brown) for 5/5 mice a splenomegaly was present for 2/5 mice liver was colorless (clear brown) for 5/5 mice other organs (intestines, heart, skin, lungs, stomach, brain) were similar to control group |
| group 4: DC101 + biocompatible nanoparticles No. 2, injection 4 h after (5 mice) | Compared to control group (group 1): a splenomegaly was present for 1/5 mice liver was little colorless for 2/5 mice other organs (kidneys, intestines, heart, skin, lungs, stomach, brain) were similar to control group |
| group 5: DC101 + biocompatible nanoparticles No. 2, injection 24 h after (5 mice) | all organs were normal during necropsy for 5/5 mice, i.e., similar to control group |
| group 6: biocompatible nanoparticles No. 2 (5 mice) | all organs were normal during necropsy for 5/5 mice, i.e., similar to control group |
| group 7: DC101 + biocompatible nanoparticles No. 1, injection 4 h after (4 mice) | Compared to control group (group 1): a splenomegaly was present for 1/4 mice other organs (liver, kidneys, intestines, heart, skin, lungs, stomach, brain) were similar to control group |

Group 2 (DC101 alone) presents visual signs of toxicity on the liver, spleen and kidneys. Of note, blood sampling performed during the tumor growth delay assay showed an increase of blood viscosity for all mice of group 2.

Interestingly, it has been observed that VEGFR2 (vascular endothelial growth factor receptor 2) selective blockage by DC101 induces an increase of erythropoietin (EPO) expression by liver (Nature Medicine vol. 12, N 7, July 2006, pp 793-800). Increase of EPO production leads to an increase of the production of red blood cells and subsequently to an increase of hematocrit. The increase of number of red blood cells as well as hematocrit increase have been correlated with VEGFR2 inhibition by DC101 (Nature Medicine vol. 12, N 7, July 2006, pp 793-800).

Hematocrit increase with an increase of EPO production is correlated with a secondary erythrocytosis (Nature Medicine vol. 12, N 7, July 2006, pp 793-800). It is established that cases of erythrocytosis, due to the increased red blood cell number, present most of time a splenomegaly (Clin. Lab. Haem. Vol. 21, pp 309-316, 1999). Another cause of secondary erythrocytosis can be renal lesions such as cysts (Clin. Lab. Haem. Vol. 21, pp 309-316, 1999). It has been shown that inhibition of VEGFR2 by DC101 leads to renal cyst formation in mice (Kidney Inter. Vol. 69, pp 1741-1748, 2006) in addition to other renal failure such as proteinuria occurring with anti-angiogenic antibodies (Jpn J. Clin. Oncol. Vol. 43, No. 6, pp 587-595, 2013).

Based on available DC101 literature, observations made during necropsy on group 2 (DC101 alone) can be related to the off-target toxicity of the anti-angiogenic monoclonal antibody DC101. This conclusion is supported by control vehicle group (group 1) and group 6 (biocompatible nanoparticles No. 2) for which no signs of toxicity were observed during necropsy.

Surprisingly inventors observed a marked decrease of toxicity (as assessed by clinical observation of the organs during necropsy of animal) in animals of groups 4 and 7. Even more surprising, no toxicity is observed in all animal of group 5.

Conclusion: The combination of DC101 with biocompatible nanoparticles from Example 1, intravenously injected 4 hours after DC101 injection, is able to preserve DC101 anti-tumor efficacy with a marked decrease of toxicity of DC101 treatment. Of utmost interest, the combination of DC101 with biocompatible nanoparticles from Example 1, intravenously injected 24 hours after DC101 injection, is able to preserve DC101 anti-tumor efficacy and to completely abolish the toxicity of DC101 treatment (when evaluated through visual observation of the main organs of the animals at the time of necropsy).

Therefore the biocompatible nanoparticle of the invention, comprising at least one oligomer of albumin (n≥2) or consisting of an oligomer of albumin, can efficiently reduce unwanted normal tissue toxicities of antibodies (such as DC101), when said at least one oligomer is administered after the antibody in a subject in need of said antibody compound.

Example 6

Preparation of the at Least One Biocompatible Nanoparticle, Said Biocompatible Nanoparticle Comprising at Least One Oligomer of Albumin (n≥2) (See FIG. 2m), with Mean Particle Size Typically of about 50 nm Mouse Serum Albumin (0.8 g) was dissolved in 10 mL of 100 mM phosphate-buffered saline (PBS) pH 7.4. The solution was mixed with 2.4 mL of a freshly aqueous 4arm-Poly (Ethylene glycol)-Maleimide 11 kDa solution (5 mM). After adjusting the pH to 8.2, the sample was incubated at room temperature during 24 h. Subsequently, the resulting suspension was conserved at pH 9. Final concentration of albumin was determined using the BCA Assay and found equal to about 64 g/L.

Example 7

Characterization of the at Least One Biocompatible Nanoparticle Consisting of an Oligomer of Albumin (n≥2) in the Suspension of Example 6

Presence of nanoparticles consisting of at least one oligomer of albumin was checked by electrophoresis. 7.5 µL of suspension of mouse serum albumin (MSA) (albumin 0.5 g/L), of suspension from Example 1 (albumin 0.5 g/L), and of suspension from Example 6 were mixed with 2.5 µL of a solution of Lithium Dodecyl Sulfate (LDS) sample loading buffer (4×). A non-denaturating 4-12% gradient polyacrylamide gel was cast in the XCell SureLock vertical electrophoresis and run at 200V for 1h50.

Typically, the proportion of oligomer is evaluated by separation by size exclusion chromatography on a superose 6 column followed by subsequent dosage of albumin in each fraction with the Bradford method, size evaluation in each fraction by dynamic light scattering (DLS) and molecular weight evaluation on each fraction by gel electrophoresis on a non-denaturating 4-12% gradient polyacrylamide gel.

Figure 7:
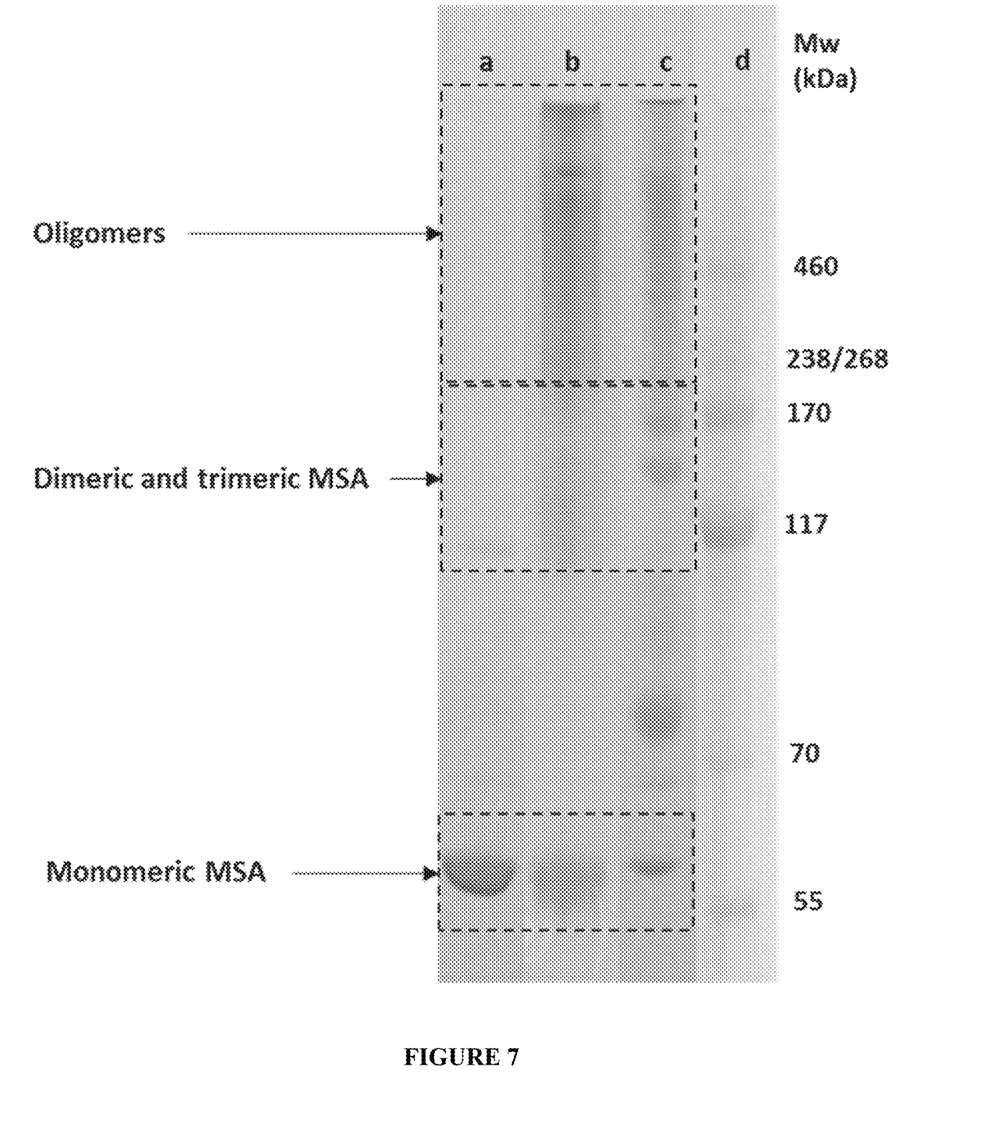
FIG. 7: Gradient polyacrylamide electrophoresis gel with:
(a): a suspension of mouse serum albumin (MSA), i.e., a suspension of biocompatible nanoparticles No. 1 (see Example 2);
(b): a suspension of MSA prepared according to example 1, i.e., a suspension of biocompatible nanoparticles No. 2 (see Example 2);
(c): a suspension of MSA prepared according to example 6, i.e., a suspension of biocompatible nanoparticles No. 3 (see Example 7); and
(d): HiMark Protein standard 31-460 kDa.

The results presented in FIG. 7 show that:

The MSA suspension (FIG. 7, line a) as such contains a low fraction of oligomers (n≥2) of albumin (suspension of biocompatible nanoparticles No. 1). About 10% of the collected albumin was identified as oligomers of albumin with molecular weights comprised equal to about 120 kDa (n=2) (of note albumin monomer molecular weight is equal to about 66 kDa). The mean particle size of the biocompatible nanoparticles in suspension was measured by dynamic light scattering (DLS) using a zetasizer NanoZS (Malvern Instrument) with a 633 nm HeNe laser at an angle of 173°. The mean particle size of the biocompatible nanoparticles in suspension was equal to about 9 nm with a polydispersity index (PDI) of 0.207.

The suspension from Example 1 (FIG. 7, line b) contains a larger proportion of oligomers of albumin (suspension of biocompatible nanoparticles No. 2) when compared to the MSA suspension. About 50% of the collected albumin was identified as oligomers of albumin with molecular weights comprised between about 120 kDa (n=2) and about 1300 kDa (n=20) (of note albumin monomer molecular weight is equal to about 66 kDa). The mean particle size of the biocompatible nanoparticles in suspension was measured by dynamic light scattering (DLS) using a zetasizer NanoZS (Malvern Instrument) with a 633 nm HeNe laser at an angle of 173°. The mean particle size of the biocompatible nanoparticles in suspension was equal to about 30 nm with a polydispersity index (PDI) of 0.250.

The suspension from Example 6 (FIG. 7, line c) contains a larger proportion of oligomers of albumin (suspension of biocompatible nanoparticles No. 3) when compared to the MSA suspension and the suspension of biocompatible nanoparticles No. 2. About 70% of the collected albumin was identified as oligomers of albumin with molecular weights comprised between about 120 kDa (n=2) and about 1300 kDa (n=20) (of note albumin monomer molecular weight is equal to about 66 kDa). The mean particle size of the biocompatible nanoparticles in suspension was measured by dynamic light scattering (DLS) using a zetasizer NanoZS (Malvern Instrument) with a 633 nm HeNe laser at an angle of 173°. The mean particle size of the biocompatible nanoparticles in suspension was equal to about 50 nm with a polydispersity index (PDI) of 0.475.

We claim:

1. A therapeutic method comprising a step of administering at least one pharmaceutical compound to a subject having a disease or disorder selected from a cardiovascular disease, a central nervous system disease, a cancer, an infectious disease or a metabolic disorder with said at least one pharmaceutical compound and a distinct step of administering at least one biocompatible nanoparticle to said subject, wherein the at least one pharmaceutical compound comprises an IgG antibody or an antigen binding fragment thereof, a crystallizable IgG-fragment (IgG Fc), or a fusion protein; the at least one biocompatible nanoparticle consists of albumin monomers conjugated to each other to form at least one oligomer of albumin (n≥2) through direct interaction or via a linker that consists of maleimide, glutaraldehyde or ethylenediaminocarbodiimide (EDC), the longest or largest dimension of the at least one biocompatible nanoparticle is between about 4 nm and about 500 nm, the at least one biocompatible nanoparticle is distinct from the pharmaceutical compound and said at least one nanoparticle is administered to the subject between 5 minutes and about 72 hours after the pharmaceutical compound.

2. The method according to claim 1, wherein the at least one oligomer of albumin is a dimer of albumin (n=2), a trimer of albumin (n=3), or consists of at least 4 monomers of albumin (n≥4).

3. The method according to claim 1, wherein the at least one oligomer of albumin consists of less than 50 monomers of albumin.

4. The method according to claim 1, wherein the biocompatible nanoparticles consist of a mixture of albumin oligomers, wherein the mixture of albumin oligomers consists of at least two distinct oligomers selected from dimers of albumin (n=2), trimers of albumin (n=3) and albumin oligomers that are at least 4 monomers of albumin (n≥4).

5. The method according to claim 1, wherein the at least one pharmaceutical compound is a fusion protein, an IgG antibody or an antigen binding fragment thereof conjugated to a cytotoxic agent, an engineered antibody or a multispecific antibody.

6. The method according to claim 5, wherein the at least one pharmaceutical compound is selected from abatacept, abciximab, adalimumab, aflibercept, alefacept, alemtuzumab, basiliximab, belimumab, bevacizumab, brentuximab, canakinumab, certolizumab pegol, cetuximab, daclizumab, denosumab, eculizumab, efalizumab, etanercept, gemtuzumab ozogamicin, golimumab, infliximab, ipilimumab, natalizumab, ofatumumab, omalizumab, palivizumab, panitumumab, rituximab, tocilizumab, trastuzumab and ustekinumab.

7. The method according to claim 1, whereby the administration of the at least one biocompatible nanoparticle and of the pharmaceutical compound maintains or increases the therapeutic benefit of the pharmaceutical compound and reduces toxicity, when compared to therapeutic benefit and toxicity induced by the standard therapeutic dose of said pharmaceutical compound in the absence of biocompatible nanoparticle.

8. The method according to claim 1, wherein the at least one oligomer of albumin consists of less than 25 monomers of albumin.

* * * * *

UNITED STATES PATENT AND TRADEMARK OFFICE
CERTIFICATE OF CORRECTION

PATENT NO. : 11,191,846 B2
APPLICATION NO. : 16/051604
DATED : December 7, 2021
INVENTOR(S) : Marie-Edith Meyre et al.

Page 1 of 1

It is certified that error appears in the above-identified patent and that said Letters Patent is hereby corrected as shown below:

In the Specification

<u>Column 13,</u>
Line 49, "7.54, of" should read --7.5µL of--.

Signed and Sealed this
Twelfth Day of April, 2022

Drew Hirshfeld
*Performing the Functions and Duties of the
Under Secretary of Commerce for Intellectual Property and
Director of the United States Patent and Trademark Office*